United States Patent [19]

Ward et al.

[11] Patent Number: 5,032,615
[45] Date of Patent: Jul. 16, 1991

[54] CONTINUOUS HEMODIALYSIS USING CITRATE

[75] Inventors: David M. Ward; Ravindra L. Mehta, both of San Diego, Calif.

[73] Assignee: The Regents of the University of California, Oakland, Calif.

[21] Appl. No.: 429,397

[22] Filed: Oct. 31, 1989

[51] Int. Cl.$^5$ .................... A61K 31/19; A61K 47/00
[52] U.S. Cl. ............................. 514/574; 514/784; 514/822; 514/23; 424/678; 424/679; 424/682; 424/680
[58] Field of Search ............... 514/574, 784, 882, 822, 514/23; 210/647; 424/679, 682, 680, 678

[56] References Cited

U.S. PATENT DOCUMENTS 3,962,075  6/1976  Fialkoff et al. ............... 210/647
4,500,309  2/1985  Diederich et al. ............. 604/5

FOREIGN PATENT DOCUMENTS 0399549  11/1990  European Pat. Off. .

OTHER PUBLICATIONS

Chemical Abstracts (108:226817g) 1988.
Chemical Abstracts (109:27520a) 1988.
Morita et al., Regional Anticoagulation During Hemodialysis Using Citrate, The American Journal of the Medical Sciences, 242:32-43 (1961).
Pinnick et al., Regional Citrate Anticoagulation for Hemodialysis in the Patient at High Risk for Bleeding, The New Encland Journal of Medicine 308:258-261 (1983).
Loh et al., Regional Citrate Anticoagulation for Hemodialysis following Cardiovascular Surgery, Am. J. Nephrol. 8:368-372 (1988).
von Brecht et al., Regional ANtiocoagulation: Hemodialysis with Hypertonic Trisodium Citrate, American J. of Kidney Diseases, 8:196-201 (1986).
Hocken, A. G. and Hurst, P. L., Citrate Regional Anticoagulation in Haemodialysis Nephron 46:7-10 (1987).

Primary Examiner—Frederick E. Waddell
Assistant Examiner—Kevin E. Weddington
Attorney, Agent, or Firm—Pretty, Schroeder, Brueggemann & Clark

[57] ABSTRACT

The present invention provides a method of preventing blood from clotting in a filter during continuous arteriovenous or venovenous hemodialysis on a patient comprising administering to the blood an amount of citrate sufficient to prevent clotting in the filter. The invention preferably utilizes a dialysate having a sodium and calcium concentration below that of normal blood and an alkali concentration sufficiently low to reduce or prevent alkalosis.

18 Claims, 3 Drawing Sheets

5,032,615

CONTINUOUS HEMODIALYSIS USING CITRATE

Throughout this application various publications are referenced by numbers within parentheses. Full citations for these publications may be found at the end of the specification immediately preceding the claims. The disclosures of these publications in their entireties are hereby incorporated by reference into this application in order to more fully describe the state of the art to which this invention pertains.

BACKGROUND OF THE INVENTION

Continuous arteriovenous hemodialysis (CAVHD) is being used increasingly as the major form of renal replacement therapy for critically ill patients with acute renal failure (ARF). Generally, the procedure has required systemic anticoagulation utilizing heparin or, in a few cases, prostacyclin to maintain filter patency (1). Although heparin is removed by CAVHD membranes, systemic anticoagulation is usually unavoidable and has been associated with an increased incidence of bleeding (2). In order to circumvent this problem regional heparin anticoagulation has been tried, but this has not gained widespread acceptance due to the difficulty in accurately adjusting protamine doses (3). Similarly, CAVHD has been attempted with frequent saline flushes through the filter, but it has been difficult to keep the filter patent for longer than 24 hours. Although regional citrate anticoagulation has been utilized for conventional hemodialysis (3) it has not previously been used for CAVHD. Citrate was previously not suitable for CAVHD due to the problem of accumulation of citrate and the products of citrate metabolism when used continuously over periods of many hours or days, and the limitation on the rate of removal of these products given the low dialysate flow rates employed in CAVHD.

Thus, there exists a need for an anticoagulant which can be effective in CAVHD but not produce the increased bleeding associated with heparin. This need is satisfied by the present invention due to the development of a technique employing sodium citrate as a regional anticoagulant for CAVHD (citrate CAVHD) which results in smooth removal of excess water, electrolytes and catabolic toxins without requiring systemic anticoagulation. Citrate is infused at the origin of the extracorporeal circuit, and the citrate-calcium chelate is removed by diffusion across the membrane. The metabolic consequences of the sodium citrate load are compensated for by the use of a special dialysate containing no alkali, subnormal sodium concentration, and no calcium. Calcium homeostasis is restored by a peripheral infusion of calcium chloride.

This system achieves excellent patency and longevity of the standard CAVHD filter without any systemic anticoagulant effect. We have successfully utilized citrate CAVHD for two thousand hours in eleven critically ill patients without any hemorrhagic complications, whereas one third of patients treated with standard heparin anticoagulated CAVHD (heparin CAVHD) developed complications related to heparinization. Citrate CAVHD can replace heparin anticoagulation and is especially advantageous in seriously ill ARF patients who are at higher risk of bleeding.

SUMMARY OF THE INVENTION

The present invention provides a method of preventing blood from clotting in a filter during continuous arteriovenous or venovenous hemodialysis on a patient comprising administering to the blood an amount of citrate sufficient to prevent clotting in the filter. The invention preferably utilizes a dialysate having a sodium and calcium concentration below that of normal blood and an alkali concentration sufficiently low to reduce or prevent alkalosis.

DETAILED DESCRIPTION OF THE INVENTION

Figure 1A:
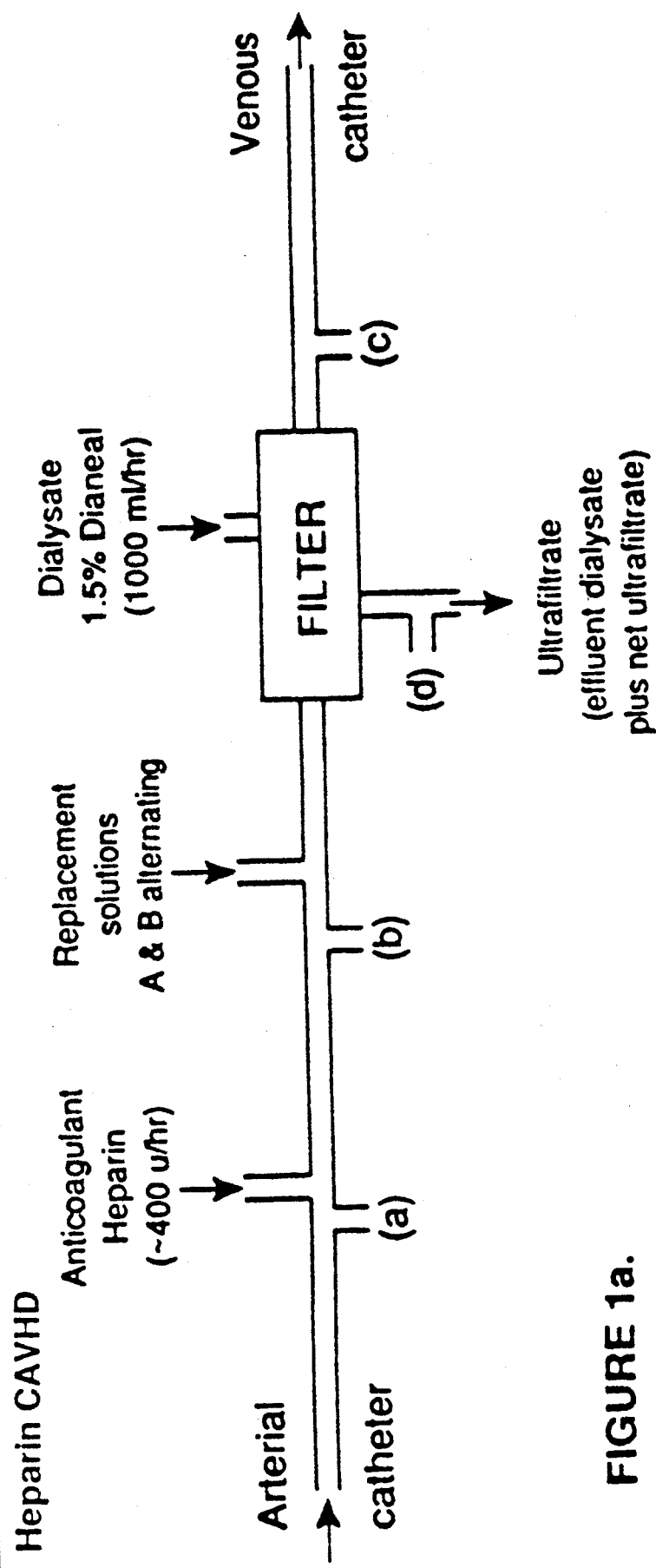
FIG. 1 shows a comparison of circuit diagrams for heparin CAVHD (FIG. 1A), and citrate CAVHD (FIG. 1B). Sampling ports are (a) "peripheral", (b) "pre-filter", (c) "post-filter", and (d) "ultrafiltrate".

The present invention provides a method of preventing blood from clotting in a filter during continuous arteriovenous or venovenous hemodialysis on a patient comprising administering to the blood an amount of citrate sufficient to reduce or prevent clotting in the filter. The citrate can occur in any suitable form but is most commonly sodium citrate. It is understood that such citrate administration is in an amount which is suitable for use in a patient, i.e., does not cause irreparable hypocalcemia, alkalosis, or hypernatremia.

In a preferred embodiment, the invention comprises administering a dialysate. The dialysate preferably has a sodium concentration below that of normal blood. By "normal blood" is meant the sodium level which is average in a subject. A sodium concentration below that of normal blood has been found to reduce the likelihood or severity of hypernatremia in CAVHD. Thus, any reduction represents an improvement in the patient's condition. The range of sodium concentration will preferably be between about 77 and 130 mEq/l, more preferably between about 97 and 117 mEq/l. However, it is recognized that individual patients and conditions may vary as to the preferred levels. By adjusting the dialysate sodium levels, the sodium level of the replacement solution can be the same as blood. This prevents wide swings in the sodium level associated with either an increased or decreased flow of replacement fluid.

Preferably the dialysate also has an alkali concentration sufficiently low to reduce or prevent alkalosis. By "alkali" is meant a bicarbonate, acetate, lactose or other suitable base. The preferred concentration depends on dialysate or citrate flow rate. Such rates can be easily monitored and the alkali concentration calculated accordingly.

Generally, an alkali concentration below about 25 mEq/l is effective in CAVHD. Preferably, the alkali concentration is below about 15 mEq/l and more preferably the alkali concentration is essentially zero. Generally, the present method is effective at dialysate flow rates of less than about 6,000 ml/hr. Preferably, the dialysate flow rate is between about 300 and 2,400 ml/hr and more preferably the dialysate flow rate is about 1000 ml/hr. However, the flow rates may vary based on practicalities of the infusion or an individual patient's needs.

The invention also provides adding an amount of an acid sufficient to reduce or prevent alkalosis in the patient. The acid can be selected from the group consisting of hydrogen chloride, arginine hydrochloride, and ammonium chloride. The acid can be administered at any point in the dialysis or directly to the patient.

The invention also provides a dialysate with an osmolality greater or equal to normal blood. Preferably, the dialysate contains dextrose but can contain any compound to create an osmolality greater or equal to that of normal blood.

Preferably the dialysate also has a calcium concentration below that of blood and more preferably the dialysate calcium concentration is essentially zero. The invention also provides replacing calcium depleted by citrate by adding calcium either post-filter or directly to the patient to reduce or prevent hypocalcemia or citrate toxicity.

METHODS

1. Patients: From December, 1988 through July, 1989, 18 patients with acute renal failure in the intensive care units at the University of California, San Diego (UCSD) Medical Center were treated with CAVHD; 8 of them also received intermittent hemodialysis (IHD). All 18 patients had multiple organ failure, required ventilator and pressor support and had marked fluid overload and catabolic ARF (Table 1). Eleven patients received citrate CAVHD, eight underwent heparin CAVHD and three had CAVHD using saline flushes for maintaining filter patency.

2. Vascular Access: Arterial access was through an 8 F, single lumen 6 or 8 inch silastic catheter (Medcomp catheter, Medcomp Corp., Harleyville, Pa.; Vygon catheter, Renal systems, Minneapolis, Minn.) inserted into the femoral artery utilizing a Seldinger technique. Venous access utilized a double lumen 14 or 16 F catheter (Vascath, Quinton Instruments, Seattle, Wash.) inserted into the femoral or subclavian vein.

3. Filter: All patients were treated with a polyacrylonitrile membrane hemofilter in a parallel plate configuration with a surface area of 0.5 sq meters (Hospal AN69S, Hospal Inc., Lincolnshire, Ill.).

4. Extracorporeal Circuit:

A) Heparin CAVHD: A schematic of the circuit used is shown in FIG. 1a. The filter was primed with two liters of heparinized saline containing 2500 U of heparin. Following an initial bolus of 5–10 U/Kg, heparin was infused prefilter at a rate of 3–12 U/Kg/hr to maintain activated clotting times (ACT), (Hemochron 400, Kentec Inc., Irvine, Calif.), between 200–350 seconds prefilter. Dialysate was Dianeal 1.5% (Baxter Corp., Deerfield, Ill.) and the dialysate flow rate was one liter/hr. The ultrafiltrate and effluent dialysate were collected in a urine bag, the height of which was adjusted to maintain an ultrafiltration rate of 400–600 ml/hour. Hourly measurements of ultrafiltrate were made and the desired net balance was achieved by replacing the excess removed with two replacement solutions given alternately. Solution A was one liter of 0.9% saline with 10 cc of 10% calcium gluconate, while Solution B was one liter of 0.45% saline with 50 cc of 7.5% sodium bicarbonate. Both replacement solutions were given pre-filter. Measurements of blood levels of electrolytes, including calcium, magnesium and phosphorus were made every 6–12 hours and any deficiencies were corrected.

Figure 1B:
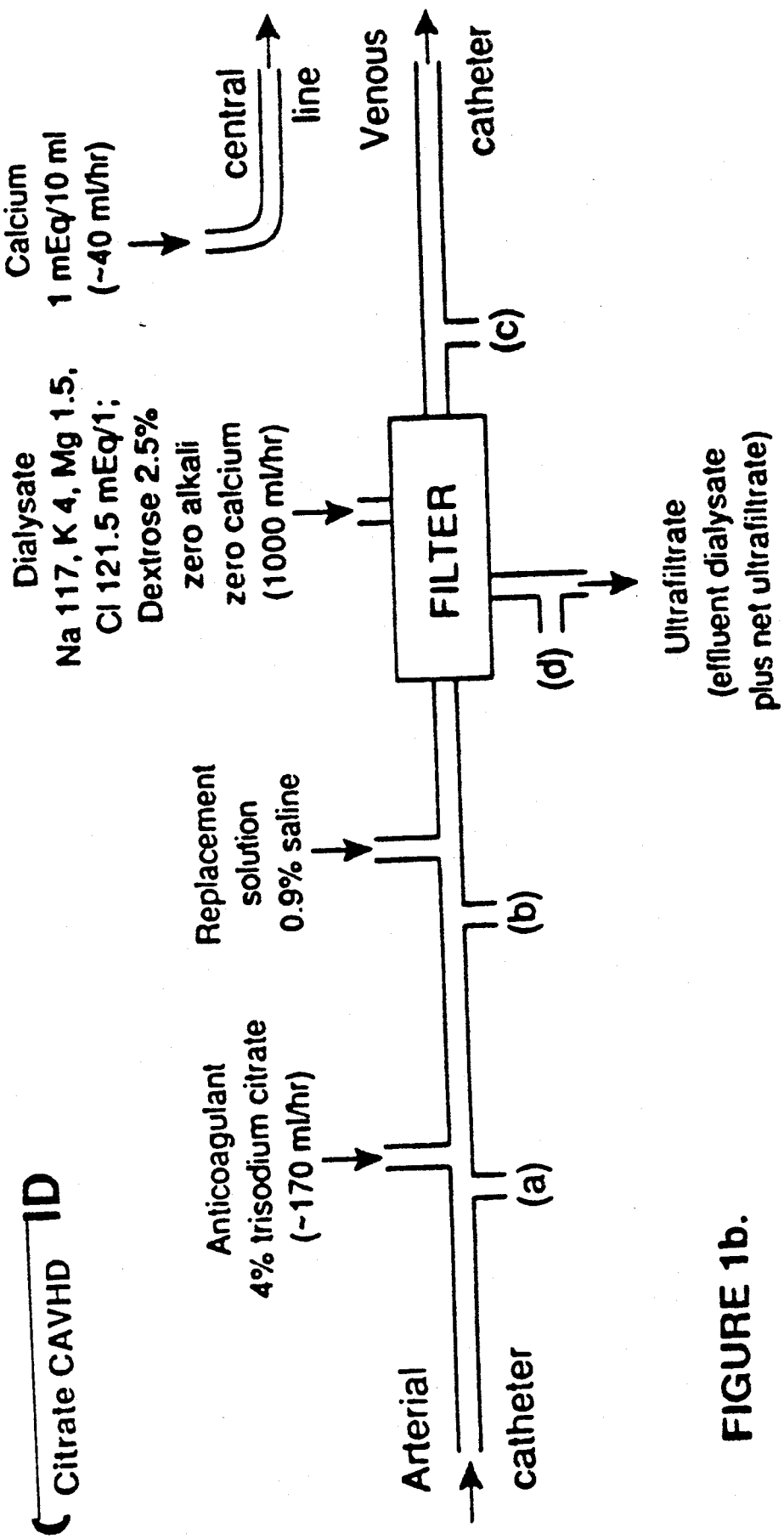

B) Citrate CAVHD: The circuit is depicted in FIG. 1b. The method used has now been standardized as follows: A 3-way stopcock is placed between the arterial catheter and the tubing connecting the filter, and 4% trisodium citrate (140 mmol citrate and 420 mmol sodium/liter, Baxter Corp., Deerfield, Ill.) is infused at this site at an initial rate of 170 ml/hr with a range of 100–200 ml/hr, depending upon the blood flow rate. The citrate flow rate is adjusted to maintain the post-filter ACT at 200–350 seconds. Generally, citrate flow rates range from 3–8% of the blood flow rate. 0.9% saline is utilized as replacement fluid and is administered pre-filter distal to the citrate infusion. The volume of replacement fluid is determined by the fluid balance required every hour. The dialysate solution is prepared from 0.45% saline, to each liter of which is added 50 ml of 50% dextrose, 4.0 mEq of potassium chloride, 1.5 mEq of magnesium sulfate and 10 mls of 23.4% sodium chloride (4 mEq per ml). The resulting dialysate contains sodium 117 mEq per liter, chloride 121.5, potassium 4.0, magnesium 1.5 and dextrose 2.5%. It contains no calcium and no alkali (alkali here means bicarbonate, acetate, lactate or other base). This dialysate is infused at a rate of 1 L per hour through the filter. Ultrafiltrate is collected in a bag, the height of which is adjusted to achieve a net ultrafiltration rate of approximately 400–600 ml/hr. Calcium is replaced via a separate central venous access using a solution comprised of 20 mls of 10% calcium chloride added to 250 mls of 0.9% saline (1 mEq of calcium per 10 mls). This is infused at an initial rate of 40 mls/hr (4 mEq/hr) with a range of 3–5 mEq/hr depending upon the level of ionized calcium and the citrate infusion rate.

5. Routine Blood Sampling and Monitoring: Routine sites for sampling are shown in FIG. 1 and include: (a) peripheral, drawn from an arterial line or the side port of the CAVHD catheter (Medcomp), or if neither of these exist, from an additional 3-way stopcock inserted proximal to the citrate infusion site. (b) Pre-filter, drawn from the stopcock distal to the citrate infusion site. The citrate infusion is continued during sampling from the pre-filter site and at all other times. (c) Post-filter, which is distal to the filter. (d) Ultrafiltrate, from a sample port and not from the bag. Blood flows are derived from hematocrit readings in pre- and post-filter samples and ultrafiltrate flow rates (4) and are done at initiation and every 12 hours. Infusion of the replacement solution is temporarily stopped while samples for blood flow and clearance studies are being drawn. Generally, clearance studies on the filter are done by standard methods at least twice a day. Both blood and dialyzer clearances are calculated. Peripheral blood electrolytes, BUN, creatinine, total and ionized calcium, phosphate and magnesium are monitored every 12 hours or more frequently as necessary. Arterial blood gases are monitored similarly.

6. Citrate measurement: Monitoring of plasma citrate levels is not necessary for routine operation of citrate-CAVHD. Citrate levels for our studies were determined using an enzymatic assay (5).

7. Citrate-CAVHD Modifications: Variation of the formulation of all infusates and dialysates is possible to accommodate special metabolic requirements. We have chosen the following methods, although others are possible, to deal with special situations as indicated: (a) In the event of systemic acidosis we give an extra infusion of bicarbonate. Alternatively, appropriate amounts of bicarbonate could be added to the dialysate or replacement solution. (b) In the event of systemic alkalosis we give a central infusion of 0.2 molar hydrochloric acid (HCl) usually at 100 ml/hr for 5-10 hrs. Acid could also be added to the citrate infusate or elsewhere. (c) In the event of hypernatremia we reduce dialysate sodium from 117 to 97 meq per liter. The alternative of lowering sodium in the replacement fluid is less efficacious in our experience. (d) Potassium or magnesium can be supplemented extraneously or altered in the dialysate formulation. (e) The glucose content of the dialysate could be varied for a variety of purposes. (f) We routinely give the calcium solution via a separate central line. We do not favor infusing calcium in the post-filter circuit because this tends to promote clotting of the venous access, particularly if the blood flow rate is very low. The alternative of administering calcium by adding it to the dialysate solution has proved troublesome in our experience (see below).

RESULTS

1. Clinical Features

The clinical characteristics of the eighteen patients with ARF are shown in Table 1. All patients were admitted to the ICU and had multiorgan failure in addition to ARF. Six of the patients received CAVHD after failing to tolerate IHD. Heparin was used as an anticoagulant for CAVHD in eight patients, two of whom were changed to citrate CAVHD because of critical heparin-induced thrombocytopenia (case #6) and life threatening bleeding (case #14). Three patients were treated with saline flushes through the filter. Two of these patients also received heparin CAVHD; one with hepatic failure (case #7) clotted his filter on saline flushes and was converted to heparin; the other is described below (case #6). Citrate anticoagulation was the sole method in nine patients and replaced heparin CAVHD in another two.

The first patient treated with citrate anticoagulation was case #6. This patient had an underlying membranous nephropathy and recurrent pulmonary emboli with debilitating cardiopulmonary failure for which he underwent a pulmonary thromboendarterectomy (6). Postoperatively he was hypotensive, fluid overloaded and oliguric with progressively worsening oxygenation. He was treated with heparin CAVHD with a rapid improvement in his hemodynamic status, but developed marked thrombocytopenia secondary to heparin induced platelet antibodies. He was subsequently treated with citrate CAVHD following a brief unsuccessful attempt at anticoagulation with prostanoid and saline flushes. Initially, the citrate anticoagulation was complicated by the development of metabolic alkalosis and hypernatremia because regular 1.5% Dianeal solution was used as the dialysate. Reducing the sodium content and eliminating bicarbonate from the replacement solution was inadequate and unstable fluctuation in serum sodium levels continued. The problem was resolved with the use of a zero-alkali, low-sodium dialysate. Also, the presence of calcium in the Dianeal solution required a higher dose of citrate for the maintenance of adequate anticoagulation (once verging on systemic citrate accumulation, revealed as an increased anion gap). When a zero-calcium dialysate was substituted, it was found reproducibly that a much lower dose of citrate would suffice. Once the standardized citrate CAVHD method was devised (as described in Methods), it was utilized successfully and smoothly in this patient until he recovered his renal function and was discharged from the hospital. Six months later he has good cardiopulmonary and renal function and an excellent level of recovery and rehabilitation.

Four patients survived, 2 with return of renal function and 2 requiring IHD. One additional patient received IHD after stabilizing on CAVHD, but subsequently died. Of the 16 patients who died, 6 had support withdrawn for a diagnosis of irreversible brain damage and 2 patients succumbed to hepatic encephalopathy.

2. Technical Adequacy

Fluid and electrolyte balance was readily achieved in all 18 patients, and BUN and creatinine levels were consistently maintained below 60 and 3.5 mg/dl respectively. Mean blood flow rates ranged from 52-125 ml/min in all patients and were not significantly different in the heparin or citrate treated groups. Ultrafiltration rates ranged between 5.6 to 14.8 ml/min. The sieving coefficient for urea was monitored every 24 hours, and if the result fell below 0.6 the filter was changed. Mean dialyzer urea clearances ranged from 18-28 ml/min.

Figure 2:
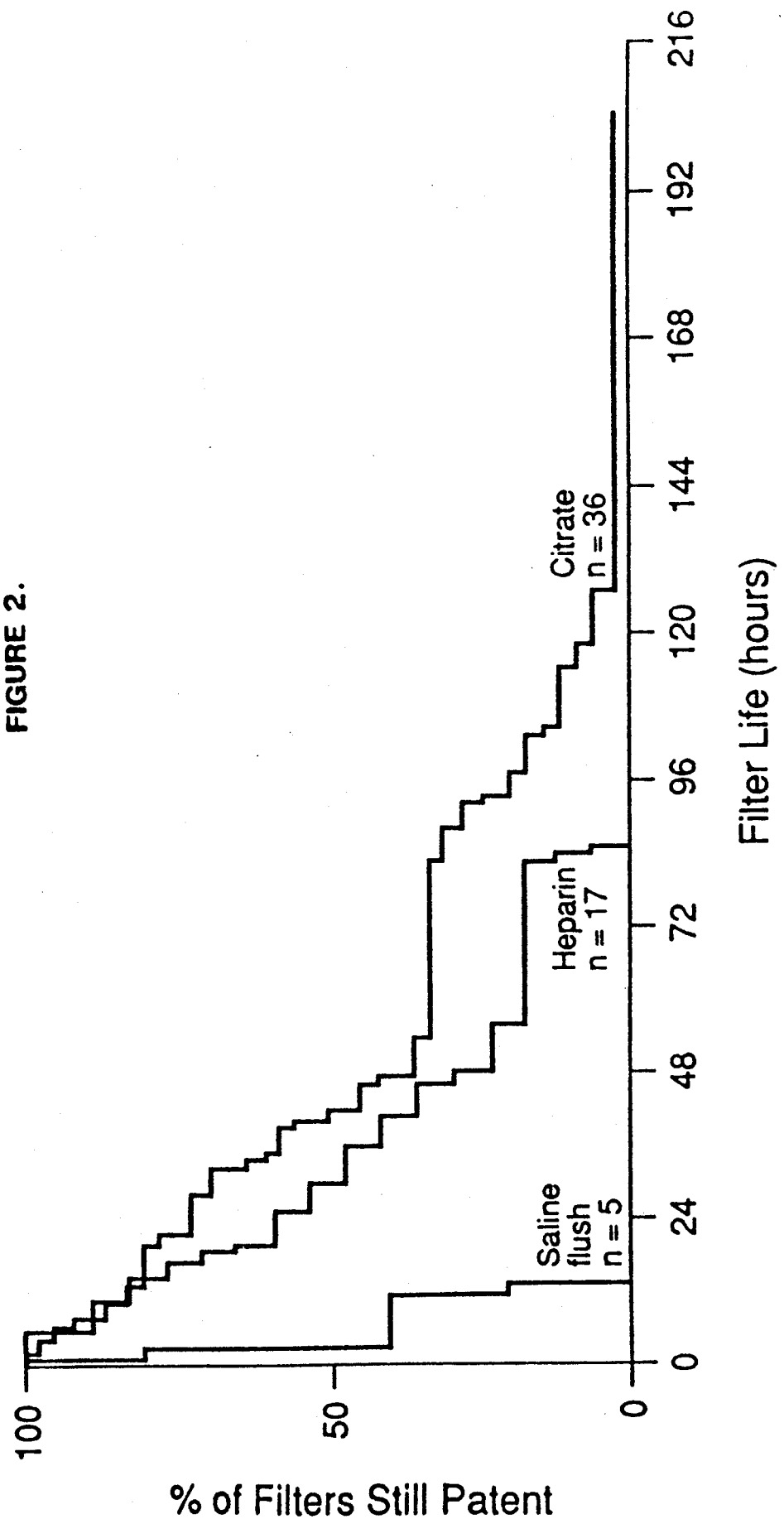
FIG. 2 shows the mean life of filters with citrate anticoagulation as compared to heparin anticoagulation and saline flushes.

A total of 2,652 hours of CAVHD was done in these 18 patients, utilizing fifty eight filters (Table 2). The mean life of filters was markedly reduced for saline flushes as compared to both heparin and citrate anticoagulation (FIG. 2). The mean filter patency for citrate anticoagulated CAVHD was significantly enhanced as compared to heparin CAVHD (55.5+7.5 hrs versus 36.53 +6.4 hrs). Filter patency ranged from 6 to 84 hours for heparin CAVHD and 5 to 207.5 hours for citrate CAVHD. 33.3% of citrate CAVHD filters were patent for longer than 72 hours while only 17.6% of heparin CAVHD filters were patent for that time. Overall 49.1% of all filters were changed due to clotting, 22.8% due to decreased efficacy, 12.3% were electively discontinued, 5.3% for access change and 12.3% due to the patient's death. There was no significant difference in the number of clotted filters for citrate CAVHD versus heparin CAVHD citrate 41.6%, heparin 47.1%) or discontinuation due to decreased efficacy (citrate 22.2%, heparin 29.4%). Filter clotting was usually seen early in the treatment course in both forms of anticoagulation and was uncommon after the first 48 hours (FIG. 2). ACT's were maintained between 200-350 seconds in both groups.

3. Complications of Treatment

Serum total and ionized calcium levels were monitored in all patients on citrate CAVHD. Peripheral ionized calcium levels ranged between 0.61 and 1.44 mmoles per liter. Symptomatic hypocalcemia did not develop in any patient. There was no evidence for any electrocardiographic changes of hypocalcemia in any patient. Peripheral serum citrate levels ranged between 0.172 and 2.95 mmoles per liter and correlated with citrate infusion rates of 120 to 210 mls per hour. There was no evidence of significant citrate toxicity in any patient although three patients transiently required HCl infusion for metabolic alkalosis related to citrate metabolism. Hypernatremia was seen only while the citrate CAVHD protocol was being developed (in case #6). Pre-existing hyponatremia transiently worsened (from 130 to 127) in one patient with hepatic dysfunction on citrate CAVHD, but was corrected by increasing the dialysate sodium.

During heparin CAVHD, two patients (25%) had serious bleeding and another (case #6) developed marked thrombocytopenia, as described above. In contrast, none of the patients while on citrate CAVHD had any episode of bleeding nor any evidence of a systemic anticoagulant effect from the citrate. Indeed, one patient (case #14), who almost died of hemorrhage while on Heparin CAVHD, and who was converted to citrate CAVHD for this reason, subsequently was twice taken to the operating room for major abdominal surgeries which were performed without complications while the citrate CAVHD continued.

DISCUSSION

The method described here for the performance of CAVHD using regional citrate anticoagulation overcomes significant problems that arise from the low blood flow rates and very low dialysate flow rates inherent in CAVHD. In contrast, conventional intermittent hemodialysis (IHD) machines employ blood flow rates in excess of 200 ml/min and dialysate flow rates of 300–700 ml/min. This allows citrate to be cleared rapidly even through conventional dialysis membranes, thus minimizing toxicity when citrate anticoagulation has been employed (7–13). In initially developing our own protocol for heparin CAVHD, we modified the technique originally described by Geronemus et al (1) to routinely include a replacement fluid infusion administered pre-filter (FIG. 1A). This, and our use of highly permeable membranes, enhanced the convective clearance obtainable with our heparin CAVHD technique, and facilitated subsequent development of our citrate anticoagulated method.

We were prompted to use regional citrate anticoagulation for CAVHD in our index patient (case #6) because other methods of anticoagulation had failed in this case. Citrate infusion was started at approximately 3–5% of blood flow rate. Use of citrate in IHD has been complicated by hypervolemia as large volumes of citrate have to be infused over a short period of time to effectively anticoagulate the extracorporeal circuit. Several investigators have used lower volumes by using a greater concentration of citrate (13). Since CAVHD requires removal of large volumes of fluid on an ongoing basis, this did not pose a significant problem for us. We were easily able to accommodate the 2.5–5 L of extra fluid infused with the citrate over 24 hrs. Citrate infusion rates provided a total load of citrate of approximately 24 mmol/hr and was adequate to maintain post-filter ACT's between 200–350 secs.

Since regional anticoagulation with citrate requires reversal of the anticoagulant effect by calcium infusion, we initially used a calcium-containing dialysate, but found that this resulted in an accumulation of citrate and calcium. This method has worked in IHD primarily because of the high dialysate and blood flow rates resulting in an increase clearance of citrate-calcium chelate. In our initial attempts with CAVHD using a calcium-containing dialysate, the dose of citrate needed to maintain adequate anticoagulation (as measured by the ACT) had to be increased to the point that verged intermittently on overt citrate toxicity as indicated by an increased anion gap. When we substituted a zero-calcium dialysate formulation, a lower dose of citrate was sufficient. This was reproducible when ACTs were measured repeatedly during 10 minute periods, alternately employing standard calcium and zero calcium dialysates. Calcium was infused into the return line or elsewhere intravenously into the patient. The latter proved superior because return of calcium into the circuit was associated with clotting when the blood flow rate was low. The required rate of calcium replenishment was first approximated by theoretical calculation, then perfected by measurement of calcium balance and by trial and error. Maintenance of calcium balance and avoidance of citrate toxicity can be adequately assured if the patient's blood levels of the following are measured every 6 hours: anion gap (Na minus Cl minus bicarb), ionized calcium and total blood calcium.

Citrate is available in a few different formulations, all based on trisodium citrate, usually pH balanced with citric acid. The sodium load imposed by citrate infusion is therefore considerable and tends to cause hypernatremia. Our initial attempt to overcome this employed low sodium or zero-sodium replacement solutions. Because the CAVHD circuit is usually capable of removing more body water per hour than the patient's needs dictate, the difference is replaced as a replacement solution, the volume calculated hourly according to the hourly fluid balance being achieved. Half-strength sodium or zero-sodium replacement solutions were found to cause unacceptably wide swings in blood sodium levels, partly because of the variable infusion rate needed for volume reasons. The degree and rapidity of swings in blood sodium so induced are potentially life threatening, or would require measurement of blood sodium at more frequent intervals than is practicable. Resolution of this problem was achieved by using full-strength physiological saline solution for the replacement solution, and by reducing the sodium content of the dialysate below the physiological level so that net sodium diffusion would remove the sodium load. Making volume replacement and sodium balance independently adjustable proved to be an important step in achieving adequate stability in our system. The required degree of reduction in dialysate sodium was calculated theoretically multiple times for different combinations of hematocrits, blood flows, citrate infusion rates and ultrafiltration rates, all of which impinge on the mass transfer of sodium to the low-sodium dialysate. It was found theoretically, and in practice, that a dialysate sodium concentration of 117 mEq/1 provided stable control of sodium balance under most conditions. If hypernatremia occurs we use another even lower formulation (sodium of 97), or combinations of 117 or 97 to achieve the desired result. This is a practical solution to the problem. In our hands the 117 sodium dialysate has been appropriate approximately 95% of the time. To ensure that the dialysate is never hypotonic we have incorporated dextrose (2.5% w/v) in all low sodium dialysates.

Citrate is metabolized in the body to bicarbonate. The continuous infusion of citrate to a patient in renal failure therefore leads to marked alkalosis which after some hours would be limiting or life-threatening (14). This trend was seen in our early attempts at citrate CAVHD. Reduction in the alkali content of the dialysate was therefore pursued, using the same mathematical approach employed to choose the sodium formulation. The result of this calculation suggested an alkali content (bicarbonate content) close to zero. The zero result is a coincidence as a different standard dialysate flow rate or different citrate flow rate would have given a different result. Employing a zero-alkali dialysate has been very successful. Minor degrees of alkalosis are still seen occasionally and we have established a protocol for reversing these with infusion of HCl. An alternative approach might be to acidify the citrate solution (more citric acid, less sodium citrate). However, this modification has not proved necessary in practice.

Following the development of our standardized protocol of citrate CAVHD, we have implemented it in a variety of critically ill patients. We have found it to be at least as effective as heparin in maintaining filter patency. Citrate levels do not need to be routinely monitored as long as citrate flow rates are adjusted to the blood flow rates and ionized calcium levels are monitored. Citrate infusions have been well tolerated, even in patients with severe hepatic dysfunction.

Utilizing our protocol, we have demonstrated that regional anticoagulation with citrate offers a practical alternative to systemic anticoagulation with heparin for CAVHD, and that it can be easily accomplished in the ICU setting to effectively achieve control of volume and solute balance. When properly monitored this technique has little chance of inducing significant patient complications and can dramatically lessen the potential for developing bleeding or thrombocytopenia. The procedure can be successfully continued during major surgery and general anesthesia. This citrate anticoagulation protocol is applicable also to pumped systems such as continuous venovenous hemodialysis (CVVHD), or indeed to any extracorporeal blood circuit in which low-flow hemodialysis occurs.

TABLE 1

| Pt. No. | Age | Sex | Condition | Anti-coag. | Days Rx | Outcome |
|---|---|---|---|---|---|---|
| 1 | 33 | M | IVDA, sepsis | H | 3.5 | Died |
| 2 | 49 | M | S/P MVR, CHF | H | 2.6 | Died |
| 3 | 29 | M | Fasciitis, sepsis | H | 5 | Lived |
| 4 | 75 | M | Necrotic bowel, sepsis | S | 1 | Died |
| 5 | 36 | M | Liver failure, sepsis | H | 1 | Died |
| 6 | 57 | M | Pulm thromboend-arterectomy | H,S,C | 13.8 | Lived |
| 7 | 61 | M | Liver failure, sepsis | S,H | 2.7 | Died |
| 8 | 32 | M | Liver failure, hemoperitoneum | C | 4.2 | Died |
| 9 | 38 | M | Pulm thromboend-arterectomy | C | 2 | Died |
| 10 | 35 | M | GI bleed, liver fail, sepsis | C | 7.3 | Died |
| 11 | 41 | M | Perirectal abscess, sepsis | C | 5.1 | Died |
| 12 | 63 | F | S/P Whipple, sepsis | C | 1.7 | Died |
| 13 | 43 | F | Pancreatitis, ARDS | C | 10.7 | Died |
| 14 | 62 | M | Nephrectomy, sepsis, ARDS | H,C | 38.6 | Lived |
| 15 | 29 | F | Trauma (MVA), sepsis | C | 1.4 | Died |
| 16 | 59 | M | IVDA, liver failure, sepsis | C | 1.4 | Died |
| 17 | 81 | F | Trauma (MVA) | C | 5.3 | Lived |
| 18 | 49 | F | Liver failure | H | 3.9 | Died |

Abbreviations
ARDS Adult Respiratory Distress Syndrome
CHF Congestive Heart Failure
IVDA Intravenous Drug Abuse Flush
MVA Motor Vehicle Accident
MVR Mitral Valve Replacement
S/P Status post . . .
C Citrate
H Heparin
S Saline Flush

REFERENCES

1. Geronemus R. Schneider N: Continuous arteriovenous hemodialysis: A new modality for the treatment of acute renal failure. Trans Am Soc Artif Int Organs. 30:610, 1984.
2. Lauer A, Sacaggi A, Ronco C, Belledonne M. Glabman S, Bosch JP: Continuous arteriovenous hemofiltration in the critically ill patient. Ann Intern Med 99:455, 1983.
3. Golper TA, Ronco C, Kaplan AA: Continuous Arteriovenous Hemofiltration: Improvements, Modifications, and Future Directions. Seminars and Dialysis 1:50, 1988.
4. Rabetoy GM, Mosley CA, Duke MS, Price CA: Continuous arteriovenous hemofiltration. Dialysis and Transplantation 18:120, 1989.
5. Warty VW, Busch RP, Virgi MA: A kit for citrate in foodstuffs adopted for assay of serum and urine. Clin Chem 30:1231, 1984.
6. Moser KM, Daily PO, Peterson KL, Dembitsky W, Vapnek JM, Shure D, Utley J, Archibald C: Thromboendartectomy for chronic major vessel thromboembolic pulmonary hypertension in 42 patients: Immediate and long term results. Ann Int Med 107:560, 1987.
7. Morita Y, Johnson RW, Dorn RE, Hall DS: Regional anticoagulation during hemodialysis using citrate. Am J. Med Sci. 242:32, 1961.
8. Pinnick RV, Wiegmann TB, Diederich DA: Regional citrate anticoagulation for hemodialysis in the patient at high risk for bleeding. N Eng J Med 308:258, 198
9. Lindsay RM, Smith AM: Practical use of anticoagulants. Page 269. In Replacement of Renal Function by Dialysis. Maher JF (editor), 3rd edition. Kluwer Academical Publishers, Dordrecht, Holland, 1989.
10. Lohr JW, Slusher S, Diederich DA: Regional citrate anticoagulation for hemodialysis following cardiovascular surgery. Am J Nephrol 8:368, 1988.
11. Boyd LM, Felton SE, Highfill BK, Underhill VL: Regional citrate anticoagulation: A report of 10 month's experience. J Nephrol Nursing, page 162, July/August, 1985.
12. Von Brecht JH, Flanigan MJ, Freeman RM, Lim VS: Regional Anticoagulation: Hemodialysis with hypertonic trisodium citrate. Am J Kidney Dis 8:196, 1986.
13. Hocken AG, Hurst PL: Citrate regional anticoagulation in haemodialysis. Nephron 46:7, 1987.
14. Kelleher SP, Schulman G: Severe Metabolic Alkalosis Complication Regional Citrate Hemodialysis. Am J Kidney Dis 9:235, 1987.

What is claimed is:

1. A method of preventing blood from clotting in a filter during continuous arteriovenous or venovenous hemodialysis on a patient comprising continuously administering to the blood which has been drawn from the patient and has not yet entered the filter an effective anti-clotting amount of sodium citrate sufficient to prevent clotting in the filter and a dialysate comprising sodium at a concentration between about 77 and 130 mEq/l, alkali at a concentration below about 25 mEq/l, calcium at a concentration below that of blood, and wherein the dialysate flow rate is less than about 6,000 ml/hr.

2. The method of claim 1, wherein the sodium is at a concentration between about 97 and 117 mEq/l.

3. The method of claim 1, wherein the dialysate has an alkali concentration sufficiently low to reduce or prevent alkalosis.

4. The method of claim 1, wherein the alkali concentration is below about 15 mEq/l.

5. The method of claim 4, wherein the alkali concentration is essentially zero.

6. The method of claim 1, wherein the dialysate flow rate is between about 300 and 2,400 ml/hr.

7. The method of claim 6, wherein the dialysate flow rate is about 1000 ml/hr.

8. The method of claim 1, further comprising adding a therapeutically effective amount of an acid sufficient to reduce or prevent alkalosis in the patient.

9. The method of claim 8, wherein the acid is selected from the group consisting of hydrogen chloride, arginine hydrochloride, and ammonium chloride.

10. The method of claim 1, further comprising a dialysate with an osmolality greater or equal to normal blood.

11. The method of claim 10, wherein the dialysate contains dextrose.

12. The method of claim 1, further comprising administering a replacement solution having about the same sodium concentration as the blood.

13. The method of claim 1, wherein the dialysate calcium concentrate is essentially zero.

14. The method of claim 1, further comprising adding sufficient calcium either post-filter or directly to the patient to reduce or prevent citrate toxicity or diminish hypocalcemia.

15. A dialysate solution comprising a sodium concentration between about 77 and 130 mEq/1, a calcium concentration below that of blood, and an alkali concentration below about 25 mEq/1.

16. The dialysate of claim 15, further comprising a glucose or dextrose concentration of about 2.5%.

17. The dialysate of claim 15, further comprising a magnesium concentration of about 1.5 mEq/1.

18. The dialysate of claim 15, further comprising a potassium concentration of about 4.0 mEq/1.

* * * * *